(12) United States Patent
Chaudhuri

(10) Patent No.: US 6,936,735 B2
(45) Date of Patent: Aug. 30, 2005

(54) PHOTOSTABLE CATIONIC ORGANIC SUNSCREEN COMPOUNDS AND COMPOSITIONS OBTAINED THEREFROM

(75) Inventor: Ratan K. Chaudhuri, Lincoln Park, NJ (US)

(73) Assignee: EMD Chemicals, Inc., Gibbstown, NJ (US)

( * ) Notice: Subject to any disclaimer, the term of this patent is extended or adjusted under 35 U.S.C. 154(b) by 245 days.

(21) Appl. No.: 10/227,943

(22) Filed: Aug. 27, 2002

(65) Prior Publication Data

US 2004/0057911 A1 Mar. 25, 2004

(51) Int. Cl.⁷ .......................... C07C 233/05; A61K 7/42
(52) U.S. Cl. ................ 564/156; 564/169; 558/401; 424/59; 424/60; 424/70.9; 424/70.11; 424/400; 424/401; 424/402; 252/8.57; 252/8.81; 132/276; 106/15.05
(58) Field of Search ................ 564/156, 169; 558/501, 401; 424/59, 60, 70.11, 70.9; 252/8.57, 8.81; 132/276; 106/15.05

(56) References Cited

U.S. PATENT DOCUMENTS

| | | |
|---|---|---|
| 3,256,312 A | 6/1966 | Strobel et al. |
| 3,272,855 A | 9/1966 | Strobel et al. |
| 3,275,520 A | 9/1966 | Strobel et al. |
| 3,278,448 A | 10/1966 | Lauerer et al. |
| 3,470,233 A | 9/1969 | Hans-Joachin et al. |
| 3,535,424 A | 10/1970 | Fjimoto et al. |
| 3,860,598 A | 1/1975 | Rosenkranz et al. |
| 3,928,324 A | 12/1975 | Rosati |
| 3,928,429 A | 12/1975 | El-Chahawi et al. |
| 4,335,054 A | 6/1982 | Blaser et al. |
| 4,457,911 A | 7/1984 | Conner et al. |
| 4,504,419 A | 3/1985 | Dexter et al. |
| 4,515,774 A | 5/1985 | Conner et al. |
| 4,592,906 A | 6/1986 | Baker |
| 4,613,499 A | 9/1986 | Conner |
| 4,647,589 A | 3/1987 | Valone |
| 4,726,942 A | 2/1988 | Lang et al. |
| 4,797,493 A | 1/1989 | Matsuno et al. |
| 4,971,996 A | 11/1990 | Shiraishi et al. |
| 4,985,237 A | 1/1991 | Matsuno et al. |
| 5,057,538 A | 10/1991 | Shiraishi et al. |
| 5,063,243 A | 11/1991 | Cho et al. |
| 5,124,354 A | 6/1992 | Green |
| 5,175,340 A | 12/1992 | Forestier et al. |
| 5,177,259 A | 1/1993 | Connor et al. |
| 5,185,370 A | 2/1993 | Backström et al. |
| 5,218,000 A | 6/1993 | Usherwood et al. |
| 5,283,352 A | 2/1994 | Backström et al. |
| 5,326,785 A | 7/1994 | Cho et al. |
| 5,451,694 A | 9/1995 | Kuhn et al. |
| 5,478,856 A | 12/1995 | Suzuki et al. |
| 5,514,711 A | 5/1996 | Kitano et al. |
| 5,516,838 A | 5/1996 | Fujiki et al. |
| 5,538,716 A | 7/1996 | Forestier et al. |
| 5,601,811 A | 2/1997 | Gallagher et al. |
| 5,654,465 A | 8/1997 | Qian et al. |
| 5,670,140 A | 9/1997 | Deflandre et al. |
| 5,738,842 A | 4/1998 | Raspanti et al. |
| 5,817,862 A | 10/1998 | Poetsch et al. |
| 5,830,441 A | 11/1998 | Wang et al. |
| 5,888,481 A | 3/1999 | Horn et al. |
| 5,951,968 A | 9/1999 | Forestier et al. |
| 6,066,327 A | 5/2000 | Gubermic et al. |
| 6,090,374 A | 7/2000 | Habeck et al. |

FOREIGN PATENT DOCUMENTS

| | | |
|---|---|---|
| DE | 28 16 819 | 10/1979 |
| EP | 0 165 710 | * 12/1985 |
| EP | 0 631 177 | 12/1994 |

OTHER PUBLICATIONS

XP-002218456, Abstract of JP 01 013017 A (Pola Kasei Kogyo KK), Jan. 17, 1989.
XP-002218455 Knoevenagel, E. et al., Chem Ber. vol. 37, 1904, pp. 4476-4482.
XP 000445674-Wright, M. E. et al., "Organic NLO Polymers 2. A Study of Main-Chain and Guest-Host Kappa(2)NLO Polymers: NLO-Phore Structure Versus Poling" Macromolecules, American Chemical Society, Easton, U.S., vol. 27, No. 11, May 23, 1994, pp. 3009-3015.

(Continued)

*Primary Examiner*—Shailendra Kumar
(74) *Attorney, Agent, or Firm*—Millen, White, Zelano & Branigan, P.C.

(57) ABSTRACT

Compounds of Formula I:

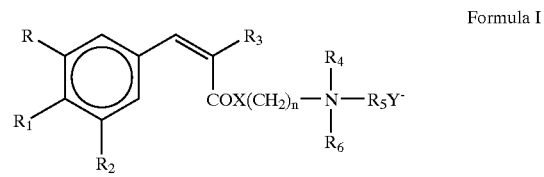

Formula I wherein

R, $R_1$ and $R_2$ are each independently hydrogen or linear or branched $C_1$ to $C_{10}$ alkyl, or linear or branched $C_1$ to $C_{10}$ alkoxy;

$R_3$ is selected from the group consisting of $COCH_3$, $CO_2R_7$, $CONH_2$, $CON(R_8)_2$, CN, $COX(CH_2)n-N-(R_4)(R_5)(R_6)$, and the quaternized salt form of the formula $COX(CH_2)n-N-(R_4)(R_5)(R_6)^+Y^-$;

X is O or NH;

n is an integer of 1 to 5;

Y is an anion;

$R_4$, $R_5$ and $R_6$ are independently linear or branched $C_1$ to $C_{30}$ alkyl; and $R_7$ and $R_8$ are independently hydrogen or linear or branched $C_1$-$C_{30}$ alkyl.

Sunscreen formulations containing compounds of Formula I, and methods for protecting hair, skin and substrates such as polymers, textiles, fabrics, leathers and paints using the compounds herein.

50 Claims, No Drawings

OTHER PUBLICATIONS

XP 002048362–Gazit A., et al., "Tyrphostins 1: Synthesis and Biological Activity of Protein Tyrosine Kinase Inhibitors" Journal of Medicinal Chemistry, American Chemical Society, Washington, U.S., vol. 32, No. 19, 1989, pp. 2344–2352.

XP–002193484–Sohda T. et al., "Antiulcer Activity of 5–Benzylthiazolidine–2,4–dione Derivatives" Chemical and Pharmaceutical Bulletin, Pharmaceutical Society of Japan, Tokyo, JP, vol. 31, No. 2, Feb. 1983 pp. 560–569.

XP 001109032–Cho, H. et al., J. Med. Chem., vol. 34, 1991, pp. 1503–1506.

Masao et al., Sunscreening and Skin–Lightening Cosmetics Containing 3,5–dimethyoxy–4–hydroxycinnamic acid and/or its Derivatives, pp. 1–2.

International Search Report, PCT/EP02/06743, Jun. 19, 2002.

CA 101:85528, Manrao et al., Evaluation of Ferulic Acid Derivatives as Antifungal Agents, Pesticides, 1984, 18 (2) pp. 30–38.

* cited by examiner

PHOTOSTABLE CATIONIC ORGANIC SUNSCREEN COMPOUNDS AND COMPOSITIONS OBTAINED THEREFROM

BACKGROUND OF THE INVENTION

Photofilters and UV-absorbers have been employed for a number of years to protect coloring dyes from fading from exposure to light. UV-sunscreens have also been employed to protect skin from damage from exposure to sunlight. Representative references related to UV-sunscreens are:

U.S. Pat. No. 5,922,310 (Chaudhuri et al.) discloses a composition which includes a cationic antioxidant phenol in an amount of about 0.01–1% wt/wt.

U.S. Pat. No. 5,427,773 (Chaudhuri et al.); U.S. Pat. No. 5,427,774 (Chaudhuri et al.); and U.S. Pat. No. 5,451,394 (Chaudhuri et al.) discloses non-hydrolysable, non irritating, hair, skin and textile substantive quaternary salts of p-dialkylaminobenzamides.

U.S. Pat. No. 5,633,403 (Gallagher et al.) discloses substantive UV-absorbing cinnamido amine cationic quaternary salts.

U.S. Pat. No. 5,830,441 (Wang et al.) discloses a photostable UV absorbent with maximum absorption above 340 nm.

Recently, sunscreens also have been added to hair care products to guard against the deleterious effects of solar irradiation on the hair. Two sunscreens have been developed especially for hair, Escalol® HP 610 (U.S. Pat. No. 5,451,394) and Incroquat® UV-283 (U.S. Pat. No. 5,633,403). Unfortunately, they both suffer from inadequate photostability, meaning that they degrade in the presence of light, and they lack desired hair substantivity, meaning that they can not be effectively applied and retained on hair.

The ideal sunscreen formulation for hair or skin should be nontoxic and non-irritating to the skin tissue and be capable of convenient application in a uniform and continuous film. The product should be chemically and physically stable so as to provide an acceptable shelf life upon storage. It is particularly desirable that the preparation should retain its protective effect over a prolonged period after application. The product must be substantive to hair or skin so that it does not get washed-off quickly. Thus, the active agent when present on the hair or skin must be resistant to chemical and/or photodegradation and be substantive.

Techniques for stabilizing UV absorbent compositions are known. Representative disclosures in this area include U.S. Pat. Nos. 5,567,418, 5,538,716, 5,951,968 and 5,670,140.

SUMMARY OF THE INVENTION

There is provided by the present invention compounds with sunscreen activity, i.e. they are chromophoric within the ultra violet radiation range of from 290–400 nm. The sunscreen formulations of this invention preferably offer protection from UV radiation with wavelengths of about 290 nm to 400 nm and preferably from wavelengths in the range of about 290–370 nm. Sunscreen formulations of this invention also typically have a sunscreening protection factor (SPF) range of from about 2 to 60, with a preferred SPF range of from about 10 to about 45. The target SPF range can be achieved with a combination of both inorganic and organic chromophoric compounds. SPF is determined by techniques well known in the art, on human skin as described in the Federal Register, Aug. 25, 1978, Vol.43, No.166, pages 38259–38269 ([]Sunscreen Drug Products for Over-The-Counter Human Use[], Food and Drug Administration). SPF values can also be approximated using in-vitro models as described, for example, in J. Soc. Cosmet. Chem. 44:127–133 (May/June 1989).

The compounds of the invention herein are represented by the general Formula I:

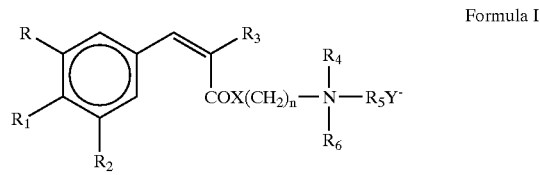

Formula I

In Formula I,

R, $R_1$ and $R_2$ are each independently hydrogen or linear or branched $C_1$ to $C_{10}$ alkyl, or linear or branched $C_1$ to $C_{10}$ alkoxy;

$R_3$ is selected from the group consisting of $COCH_3$, $CO_2R_7$, $CONH_2$, $CON(R_8)_2$, $CN$, $COX(CH_2)n-N-(R_4)(R_5)(R_6)$, and the quaternized salt form of the formula $COX(CH_2)n-N-(R_4)(R_5)(R_6)^+Y^-$;

X is O or NH;

n is an integer of 1 to 5;

Y is an anion;

$R_4$, $R_5$ and $R_6$ are independently linear or branched $C_1$ to $C_{30}$ alkyl; and $R_7$ and $R_8$ are independently hydrogen or linear or branched $C_1$–$C_{30}$ alkyl.

Preferred compounds of Formula I for hair and other substrate protection are illustrated by Formula II:

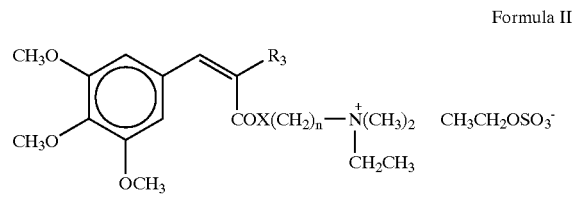

Formula II

In Formula II, $R_3$ is as defined for Formula I but is preferably $COCH_3$ or $CONH(CH_2)_3N^+(CH_3)_2(CH_2CH_3)$ $CH_3CH_2OSO^-_3$; and X is O or NH.

Concerning Formulae I and II, the integer n is preferably 2 to 3; and the anion Y is preferably Cl, Br, alkyl sulfate, alkyl sulfonate, or p-tolyl sulfonate. $R_4$, $R_5$ and $R_6$ of formulae I and II are preferably independently linear or branched $C_1$ to $C_8$. $R_7$ and $R_8$ are preferably $C_1$ to $C_8$ alkyl.

The invention is also directed to sunscreen formulations containing the compound of the invention. The compound is typically used as a protective ingredient in the sunscreen formulations against UV-A rays, UV-B rays, or both against UV-A and UV-B rays. The formulatin can contain a single compound of formula I or a mixture of compounds of formula I. Amounts of compounds of formula I typically range from 0.1 to 10 wt %, based on the weight of the sunscreen fomulation.

Preferably, the sunscreen formulation contains a compound or a mixture of compounds of the invention which are substantive and capable of protecting hair, skin or fibers against illumination in the range of about 290 to 360 nm.

It is also preferable that the compound or a mixture of compounds of the invention be capable of stabilizing the sunscreen formulation against photodegradation.

In another aspect, the invention is directed to a mixture containing at least one compound of the invention and at least one other sunscreen agent. Advantageously, the other sunscreen agent is a sunscreen agent not of Formula I, and the compound of the invention is capable of stabilizing the additional sunscreen agent against photodegradation.

In yet another aspect, the invention is also directed to a method of protecting a substrate from UV radiation by applying a compound or mixture of compounds of this invention to the substrate.

Advantageously, the substrate protected from UV radiation is hair or skin. Alternatively, the substrate protected from UV radiation is a polymer, textile fabric, leather or paint. Alternatively, the compound can be used with a hairpiece made of natural or synthetic hair to protect the hairpiece from U.V. degradation.

When the substrate is hair, an amount of the compound sufficient to improve the photostability of the hair care formulation is preferably added.

To improve the photostability of a sunscreen formulation, a compound of formula I is added to the sunscreen formulation in an amount sufficient to reduce the loss of UV absorbance of the sunscreen as it is irradiated. Typical amounts fall within the range of 0.1% to 40 wt %, based on the total weight of said sunscreen formulation. More typically, the amount falls within the range of 1 wt % to 25 wt %. The amount of organic sunscreen compound of formulae I, II, III and/or IV, preferably ranges from about 3 wt % to about 15 wt % of the sunscreen formulation. Other ingredients referred to above and discussed more particularly below are generally used in an amount from about 0.1 wt % to about 10 wt % of the sunscreen formulation. The balance comprises a cosmetically or pharmaceutically acceptable carrier.

The sunscreen formulations may contain dispersing agents, emulsifiers or thickening agents to assist in applying a uniform layer of the active compounds. Suitable dispersing agents for the sunscreen formulations include those useful for dispersing organic or inorganic sunscreen agents in a water phase, oil phase, or part of an emulsion, including, for example, chitosan.

Emulsifiers may be used in the sunscreen formulations to disperse one or more of the compounds or other components of the sunscreen formulation. Suitable emulsifiers include conventional agents such as, for example, glycerol stearate, stearyl alcohol, cetyl alcohol, dimethicone copolyol phosphate, hexadecyl-D-glucoside, octadecyl-D-glucoside, etc.

Thickening agents may be used to increase the viscosity of the sunscreen formulations. Suitable thickening agents include carbomers, acrylate/acrylonitrile copolymers, xanthan gum and combinations of these. The carbomer thickeners include the crosslinked CARBOPOL® acrylic polymers from B. F. Goodrich. The amount of thickener within the sunscreen formulation, on a solids basis without water, may range from about 0.001 to about 5%, preferably from 0.01 to about 1% and optimally from about 0.1 to about 0.5% by weight.

Minor optional adjunct ingredients for the sunscreen formulations to be applied to skin or hair may include preservatives, waterproofing agents, fragrances, anti-foam agents, plant extracts (Aloe vera, witch hazel, cucumber, etc) opacifiers, skin conditioning agents and colorants, each in amounts effective to accomplish their respective functions.

The sunscreen formulations may optionally contain an ingredient which enhances the waterproof properties such as, compounds that form a polymeric film, such as dimethicone copolyol phosphate, diisostearoyl trimethyolpropane siloxysilicate, chitosan, dimethicone, polyethylene, polyvinylpyrrolidone (PVP), polyvinylpyrrolidone/vinylacetate, PVP/Eicosene copolymer and adipic acids/diethylene glycol/glycerine crosspolymer etc. Waterproofing agents may be present at levels of from about 0.01 to about 10% by weight.

The sunscreen formulations may optionally contain one or more inorganic sunscreen agents as discussed above including micro fine surface treated titanium dioxide and micro fine untreated and surface treated zinc oxide. Titanium dioxide in the sunscreen compositions preferably has a mean primary particle size of between 5 and 150 nm and preferably from 10 to 100 nm. Titanium oxide may have anatase, rutile or amorphous structure. The zinc oxide in the sunscreen compositions preferably has a mean primary particle size of between 5 nm and 150 nm, preferably between 10 nm and 100 nm. Examples of modified titanium dioxide compositions include (but not limited to only one supplier):

Eusolex® T-45D (surface treated with alumina and simethicone, 45% dispersion in isononoyl isononoate);

Eusolex®T-Aqua, (surface treated with aluminum hydroxide, 25% dispersion in water);

Eusolex® TS (surface treated with aluminum stearate) and

Eusolex® T-2000 and Eusolex® T-ECO (surface treated with alumina and simethicone), all available from MERCK KGaA.

The sunscreen formulation may also contain one or more additional monomeric organic chromophoric compounds. These can either be UV-A, UV-B or broad band filters. Examples of suitable UV-A sunscreens include benzophenone derivatives, menthyl anthranilate, butyl methoxydibenzoyl methane and benzylidene-dioxoimidazoline derivatives. Examples of suitable UV-B sunscreens include cinnamate derivatives, salicylate derivatives, para-aminobenzoic acid derivatives, camphor derivatives, phenylbenzimidazole derivatives and diphenylacrylate derivatives. Examples of suitable broad-band sunscreen include benzotriazole derivatives and triazine derivatives such as anisotriazone. Others include ethylhexyltriazone and diethylhexylbutamidotriazone.

Particularly useful organic sunscreen agents that can be introduced are Avobenzone, 2-ethylhexyl p-methoxycinnamate, 4,4'-t-butylmethoxydibenzoyl methane, 2 hydroxy-4-methoxybenzophenone, octyldimethyl p-aminobenzoic acid, 2,2-dihydroxy-4-methoxybenzophenone, ethyl-4-[bis(hydroxypropyl)]

aminobenzoate, 2-ethylhexyl-2-cyano-3,3-diphenylacrylate, 2-ethylhexylsalicylate, glycerol p-aminobenzoate, 3,3,5-trimethylcyclohexylsalicylate, methylanthranilate, p-dimethylaminobenzoic acid, 2-ethylhexyl p-dimethylaminobenzoate, 2-phenylbenzimidazole-5-5-sulfonic acid, 2-(p-dimethylamino phenyl-5-sulfoniobenzoxazoic acid and mixtures thereof.

Examples of useful commercially available organic sunscreen agents that can be introduced include 2-phenylbenzimidazole-5-sulphonic acid, 2-(4-methylbenzylidene)-camphor, 4-isopropyldibenzoyl methane all of the Eusolex™ series sold by EM Industries and Merck KGaA, Darmstadt, Germany.

The sunscreen formulation may contain an antioxidant. Examples of suitable antioxidants which provide stability include p-hydroxybenzoic acid and its derivatives (ethylisobutyl, glyceryl esters of p-hydroxybenzoic acid); cumarin derivatives; flavones; hydroxy or methoxy substituted benzophenones; uric or tannic acid and its derivatives; hydroquinones.

The sunscreen formulations may also optionally contain one or more skin conditioning agents. These include humectants, exfoliants and emollients.

Humectants are polyhydric alcohols intended for moisturizing, reducing scaling and stimulating the removal of built scale from the skin. Typically polyhydric alcohols include polyalkylene glycols and more preferably alkylene polyols and their derivatives. Illustrative are propylene glycol, dipropylene glycol, polypropylene glycol, polyethylene glycol, sorbitol, 2-pyrrolidone-5-carboxylate, hydroxypropyl sorbitol, hexylene glycol, ethoxydiglycol 1,3-butylene glycol, 1,2,6-hexanetriol, glycerin, ethoxylated glycerin, propoxylated glycerin and mixtures thereof. Most preferably the humectant is glycerin. Amounts of humectant can range anywhere from 1 to 30%, preferably from 2 to 20% and optimally from about 5 to 10% by weight of the sunscreen composition.

The exfoliants suitable for use in the present may be selected from alpha-hydroxy carboxylic acids, beta hydroxycarboxylic acids and salts of these acids. Most preferred are glycolic, lactic and salicylic acids and their alkali, metal or ammonium salts.

Suitable emollients include those agents known for softening the skin or hair which may be selected from hydrocarbons, fatty acids, fatty alcohols and esters. Petrolatum is a common hydrocarbon type of emollient conditioning agent. Other hydrocarbons that may be employed include alkyl benzoate, mineral oil, polyolefins such as polydecene, and paraffins, such as isohexadecane. Fatty acids and alcohols typically have from about 10 to 30 carbon atoms. Illustrative are myristic, isostearic, hydroxystearic, oleic, linoleic, ricinoleic, behenic and eruicic acids and alcohols. Oily ester emollients may be those selected from one or more of the following, triglyceride esters, acetoglyceride esters, ethoxylated glycerides, alkyl esters of fatty acids, ether esters, polyhydric alcohol esters and wax esters. Additional emollients or hydrophobic agents include $C_{12}$ to $C_{15}$ alkyl benzoate, dioctyladipate, octyl stearate, octyldodecanol, hexyl laurate, octyldodecyl neopentanoate, cyclomethicone, dicapryl ether, dimethicone, phenyl trimethicone, isopropyl myristate, capriylic/capric glycerides, propylene glycol dicaprylate/dicaprate and decyl oleate.

The sunscreen formulations can be in the form of creams, ointments, suspensions, powders, oil, lotions, oleo alcoholic lotions, fatty gels, oleo-alcoholic gels and lotions, solid sticks, foams, emulsions, liquid dispersions, sprays and aerosols. More specific forms include: lipsticks, foundations, makeup, loose or press powder, eye blush, eye shadow and nail lacquer.

Additionally, the following compounds can be obtained:

Formula III

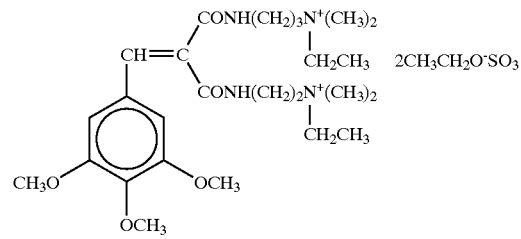

Formula IV

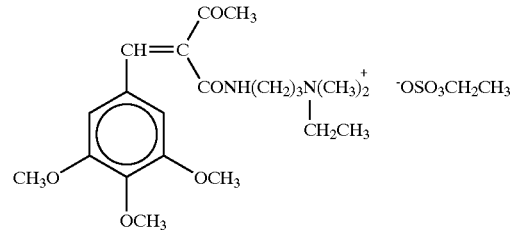

The compounds of Formulae I–IV can be obtained by condensation of a corresponding substituted benzaldehyde of the following formula:

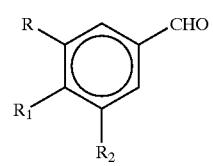

(wherein R, $R_1$ and $R_2$ are as defined above for formula I) with a compound that provides a terminal tertiary amine. An example of a compound that provides a terminal tertiary amine is a compound of the formula: $R_3$—$CH_2$—$C(O)X$ $(CH_2)_n$—$N(R_4)(R_5)$ wherein $R_3$, $R_4$,$R_5$ and X are as defined above for formula I. The tertiary amine is then quarternized with a salt of the formula $(R_6)Y$, wherein $R_6$ is as defined above for formula I. An example of a suitable salt is diethylsulfate $(CH_3CH_2)_2SO_4$.

The corresponding benzaldehyde can be obtained commercially or prepared from commercially available benzaldehydes.

Although not wishing to be bound by any specific theory, it is believed that a representative Reaction I resulting in a compound of formula I proceeds in a manner such as this:

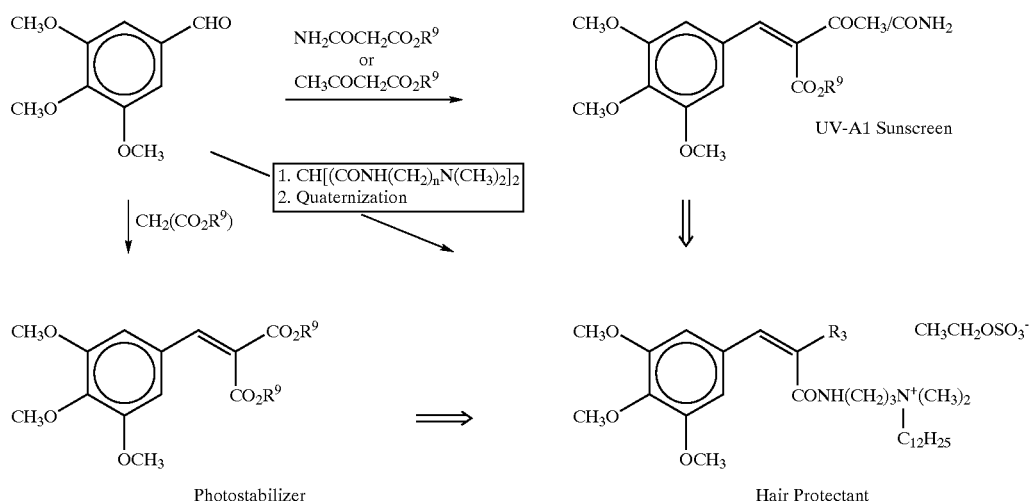

Wherein $R^9$ is $C_1$–$C_{20}$ linear or branched alkyl, such as ethyl, iso-amyl and ethylhexyl, and $R_3$ is as defined above for formula I.

Similarly, a compound of Formula I has been synthesized from the following representative Reaction II, wherein the condensation step is followed by a quaternization step.

The tertiary amine can be quaternized with diethylsulfate, p-toluene sulfonate or other salts such as $C_{12}H_{25}$ mesylate, wherein R, $R_1$ and $R_2$ are as defined above for formula I such as methoxy and t-butyl and $R^9$ is as defined above for Representative Reaction I. An example of a quaternization reaction which provides a compound of formula IV is illustrated below.

The entire disclosure of all applications, patents and publications, cited above are hereby incorporated by reference.

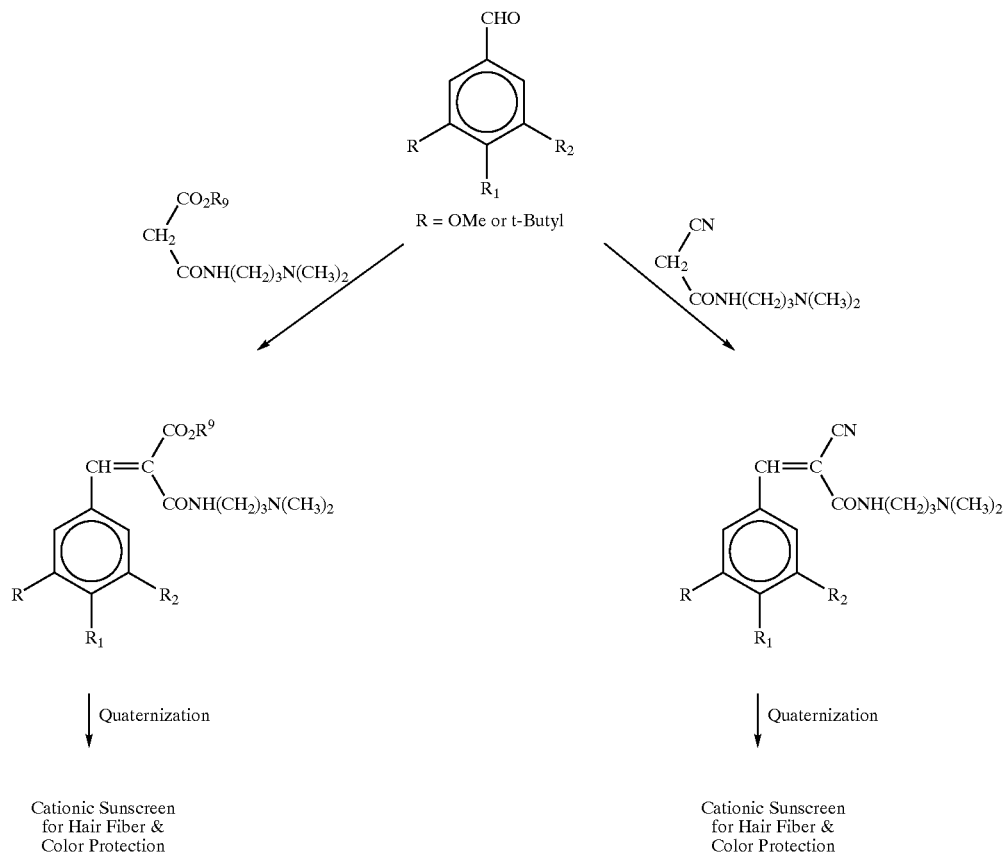

The examples below provide guidelines on how to make representative compounds of the invention.

EXAMPLES

Example I

N-(3-Dimethylaminopropyl)-alpha-acetyl-3,4,5-trimethoxy cinnamide

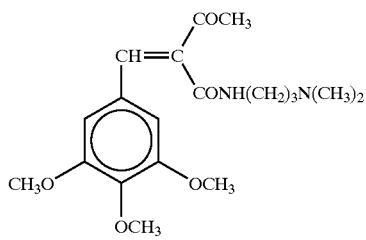

1) Condensation

N,N-Dimethylaminopropyl-alpha-acetoacetamide is yielded at 80–85% by amidation of ethyl acetoacetate using dimethyl aminopropylamine in neat condition at 90–95° C.

3,4,5-trimethoxybenzaldehyde is condensed with N,N-Dimethylaminopropyl-alpha-acetolacetamide in the presence of piperdine-acetic acid and benzene as media at reflux temperature under continuous azeotropic water removal to yield the title compound. The reaction takes about 2 hours for completion. The yield obtained is about 90%.

2) Quaternisation

The compound can be quaternized with diethylsulfate to provide a cationic sunscreen.

Example 2

N-(3-Dimethyl-3-ethylaminopropyl)-alpha-cyano-3,4,5-trimethoxy cinnamide ethyl sulphonate

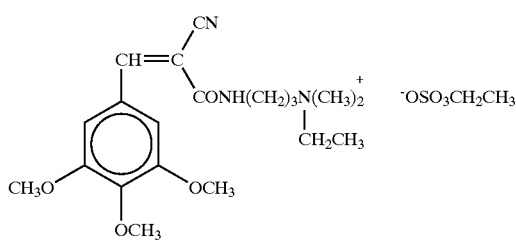

The process involves 2 steps:

1) Condensation

The N,N-Dimethylaminopropyl-alpha-cyanoacetamide is yielded at 80–85% by amidation of ethyl cyanoacetate using dimethyl aminopropylene in neat condition at 90–95° C.

3,4,5-trimethoxy benzaldehyde is condensed with N,N-Dimethylaminopropyl-alpha-cyanoacetamide in the presence of piperdine-acetic acid and benzene as media at reflux temperature under continuous azeotropic water removal. N-(3-Dimethylaminopropyl)-alpha-cyano-3,4,5-trimethoxy cinnamide is yielded. The reaction takes two hours for completion. The yield is 90%.

2) Quaternisation

The N-(3-Dimethylaminopropyl)-alpha-cyano-3,4,5-trimethoxy cinnamide is quaternised with dodecyl mesylate ($C_{12}H_{25}OSO_2CH_3$) at 100–105 degrees C. in propylene glycol as a reaction medium. The final compound is produced with a 92% yield.

Example 3

Bis-N-[3(N,N-dimethylamino)propyl]-3,4,5-trimethoxy benzylidene malonamide bis ethylsulfate Bis-N-[3(N,N-dimethylamino)propyl]-3,4,5-trimethoxy benzylidene malonamide bis ethylsulfate is prepared by condensation of 3,4,5-trimethoxy benzaldehyde and bis-N-[3-(N,N-dimethylamino)propyl]malonamide according to the following reaction scheme and procedure:

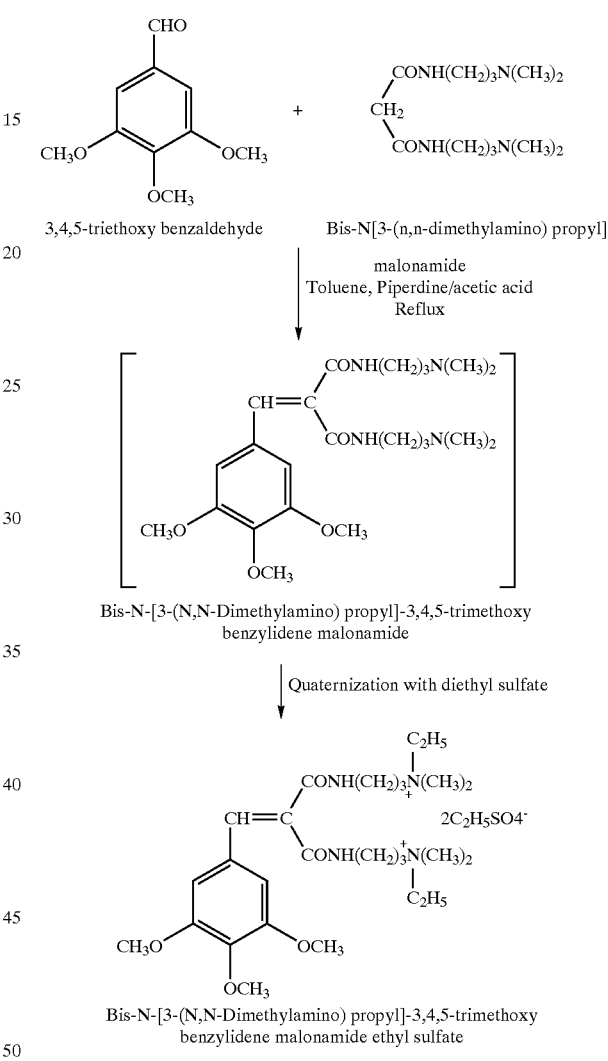

Procedure

The following are charged with stirring at room temperature: toluene (400.0 ml), 3,4,5-trimethoxybenzaldehyde (84.28 gm), bis-N-[3-(N,N-dimethylamino)propyl] malonamide (124.0 gm), piperidine (3.95 ml) and acetic acid (7.90); are heated to reflux temperature and stirred with continuous water removal for 13.5 hours. The reaction was checked by TLC (mobile phase=benzene:hexane:acetone (80:20:10)) with product detected under UV. Once product is detected, the reaction mass is cooled to 60–65 deg. C. and benzene removed under mild vacuum at 60–80 deg. C. The mass is degassed for ½ hour under vacuum at 75–80 deg. C. and nitrogen bleeding is started. The thick residue is dissolved in dimethyl formamide (200.0 ml) with stirring and cooled to 10–15 deg C.

The dissolved reaction mass is charged with diethyl sulphate (150.0 gm) at 10–15 deg C. and is heated to 85–90 deg. C. with stirring for six hours. Benzene (400.0 ml) is charged into this mixture and stirred for 10 minutes at 85–90 deg. C., after which, separate layers were allowed to form. The product layer (lower layer) was separated and washed with benzene (250 ml) at 85–90 deg. C., charged with methanol (350 ml) and charcoal (10.0 gm) at 50–55 deg. C. with stirring for one hour and then filtered through a Hydro-flow bed. The filtered layer was washed with methanol (50 ml) and distilled at 50–55 deg. C. with vacuum to remove methanol.

The mass was degassed for one hour at 90–95 deg. C. under vacuum. The yield obtained is about 85%. The product is soluble in water and has $\lambda_{max}$ 301 nm (EtOH:water—70%:30%). A 50% solution in water was prepared for ease of handling.

Example 4

Bis-N-[3(N,N-dimethlylamino)propyl]-3,4-dimethoxy benzylidene malonamide bis ethylsulfate Bis-N-[3(N,N-dimethylamino)propyl]-3,4-dimethoxy benzylidene malonamide bis ethylsulfate is prepared by following essentially the same procedure as described in Example 3, except 3,4,5-trimethoxy benzaldehyde is replaced with 3,4-dimethoxy benzaldehyde. The yield obtained is about 80%.

Photostability

The photostability of compounds of the present invention as well as existing commercial cationic sunscreens is tested according to the procedure described below:

Photostability: Comparative Photostability of Example 3, Incroquat® 283 and Escalol® HP610

Three products [Example 3 (1%), Incroquat 283 (1%) and HP610 (0.1%)] were tested for their photostability by dissolving separately in water or ethanol-water solution containing 0.1% Poly(vinylpyrrolidone-vinyl acetate) copolymer (PVP-VA S630 from ISP). Air drying on a glass plate for one hour gave a thin film, which were irradiated under UV A (2 MED/h) and UV B (1 MED/h) light separately over an 8 h period in a Q-UV Accelerated Weathering Tester. Photodegradation was calculated from the decrease in the maximum absorption of the respective products. The results are illustrated in the Tables 1 and 2.

TABLE 1

Comparative Photostability (UV-B irradiation) of Example 3, Incoquat ® UV-283 & Escalol ® HP-610

| | % Product Retained After | | |
|---|---|---|---|
| Product/Time | Initial | 1 hr | 2 hr |
| Example 3 Present Invention | 100 | 96 | 93 |
| Incroquat ® UV-283 | 100 | 36 | 28 |
| Escalol HP ®-610 | 100 | 33 | 28 |

TABLE 2

Comparative Photostability (UV-A irradiation) of Example 3, Incoquat ® UV-283 & Escalol ® HP-610

| | % Product Retained After | | | |
|---|---|---|---|---|
| Product/Time | Initial | 2 hr | 4 hr | 6 hr |
| Example 3 Present Invention | 100 | 98 | 97 | 94 |
| Incroquat ® UV-283 | 100 | 64 | 56 | 45 |
| Escalol HP ®-610 | 100 | 50 | 40 | 30 |

The results in Tables 1 & 2 clearly show that the product obtained from Example 3 has much higher photostability over the two commercially available cationic sunscreens, namely, Escalol® HP 610 and Incroquat® UV 283.

Stabilizing Activity

The stabilizing activity of the compound obtained from Example 3 toward Avobenzone is tested and compared with a conventional product according to the procedures below.

Individual solutions of selected cationic sunscreen compounds of this invention with Avobenzone were as follows. Each cationic sunscreen compound was dissolved in 50% ethanol/50% $H_2O$ solution containing roughly an equal molar amount of Avobenzone. A similar solution containing Di-2-ethylhexyl-2,6-napthalene dicarboxylic acid (DENDA) and Avobenzone was also prepared. Each solution was then illuminated in the solar simulator as configured above for the photostability tests and aliquots of each solution were removed at 30-minute time intervals. These aliquots were injected into an HPLC and the loss of Avobenzone was followed with illumination time. The high performance liquid chromatograph (HPLC) used for all experiments reported therein incorporated a Spectra-Physics model P-200 pump with an Applied Biosystems model 785A UV-Visible detector with a Rheodyne manual injector incorporating a 50 ml sample loop and a 150×4.6 mm reversed-phase $C_{18}$ column (Alltech). All analyses were carried out under isocratic elution conditions using $CH_3OH/H_2O$ mixtures for the mobile phase at a flow rate of 1 $H_2O$ ml per minute. It was necessary to employ HPLC separation of Avobenzone from each of the sunscreen compounds to quantify Avobenzone due to the absorption spectra overlap with some of these compounds.

Two formulated products [one containing Avobenzone (2% w/w) and the other one with Avobenzone+Example 3 product (2+2% w/w)] were tested for their photostability by applying samples (1–2 $\mu g/cm^2$) in between two glass plates and irradiating the samples under UV A (2 MED/h) and UV B (1 MED/h) light separately over a 6 hour period in a Q-UV Accelerated Weathering Tester. Photodegradation was calculated from the decrease in the maximum absorption of the respective products. The results show a 44% improvement in photostabilization of Avobenzone using Example 3 product.

Hair Substantivity: Comparative hair substantivity of Example 3, Incroquat® 283 and Escalol® HP610

Tests in aqueous solution: Tests are performed by using aqueous solutions of Example 3 (SCP 239) and Incroquat at 1% concentration. 100 ml aqueous solution (containing 100 mg product) are added, under constant stirring to 1 g of a slightly bleached hair swatch (cut in fine pieces less than ⅓" long). The product uptake is determined by measuring the maximal absorption of product remaining in the solute over time. The results for Example 3 and Incroquat UV-283 at 1% concentration are shown in the Table 3. Escalol® HP610 could not be tested in aqueous solution due to its very poor solubility.

Test in aqueous ethanolic solution: Example 3 and Incroquat® UV 283 have been prepared in aqueous-ethanolic solution (30:70%) at 1% concentration while a maximal concentration of Escalol® HP610 was reached at 0.25%. 100 ml of each solution is added, under constant stirring, to 1 g of a slightly bleached hair swatch under identical conditions as the previous test. The values for relative uptake of these solutions are reported in the Table 3.

TABLE 3

Comparative hair substantivity in water solution of Example 3 (present invention), and Incroquat ® UV-283

| Product/Time | % Relative Product Uptake by Hair | | | |
|---|---|---|---|---|
| | 0 min | 2 min | 5 min | 10 min |
| Example 3 | 0 | 48 | 56 | 59 |
| Incroquat ® UV-283 | 0 | 19 | 24 | 27 |

TABLE 4

Comparative hair substantivity in ethanol-water solution of Example 3 (present invention), Incroquat ® UV-283 and Escalol ® HP-610

| Product/Time | % Relative Product Uptake by Hair | | | |
|---|---|---|---|---|
| | 0 min | 2 min | 5 min | 10 min |
| Example 3 | 0 | 5 | 13 | 18 |
| Incroquat ® UV-283 | 0 | 3 | 5 | 7 |
| Escalol ® HP-610 | 0 | 2 | 3 | 3 |

For better comparison, the relative uptake of Escalol® HP610 is corrected from 0.25% solution to a 1% solution to account for the same initial weight amount as compared to the other two cationic sunscreens (100 mg of initial product present).

The results illustrated in Table 3 and 4 clearly show that the product obtained from Example 3 has much higher hair substantivity from both aqueous and aqueous-ethanolic solutions over two commercially available cationic sunscreens, namely, Escalol® HP 610 and Incroquat® UV 283.

Example 5

Shampoo Formulation

| Ingredient | % w/w |
|---|---|
| Phase A | |
| Water, deionized | 85.00 |
| Water, Sodium Laureth Sulfate, Ethoxylated Fatty Alcohol, Sodium Chloride, Sodium Sulfate | 10.00 |
| Water, sodium Chloride, Sodium Glycolate, Cocamido Propylamine, Cocamido Propyl Betaine | 3.00 |
| FD&C Green #3 or Blue #1 or Red #40 (0.1% solution) | 1.00 |
| Phase B | |
| Example 3 or 4/ Present Invention | 1.00 |
| Total | 100.00 |

Procedure:
Combine Phase A. Mix until mixture is homogeneous. Add phase B. Mix until mixture is homogeneous.

Example 6

Clear Conditioning Shampoo Formulation

| Ingredient | % w/w |
|---|---|
| Phase A | |
| Water, deionized | 75.00 |
| Sodium Laureth Sulfate (70%) | 14.00 |
| Lauramide DEA | 4.00 |
| Phase B | |
| Gafquat ® 755 N | 4.00 |
| Panthenol | 1.00 |
| Germaben II | 1.00 |
| Citric acid (25%) | Adjust pH 5–6 |
| Phase C | |
| Example 3 or 4/Present Invention | 2.00 |
| Total | 100.00 |

Procedure:

Combine Phase A and heat to 70° C. Mix until mixture is homogeneous. Add Phase B. Mix until mixture is homogeneous and cool to about 50° C. Add Phase C to the above mixture and stir well.

Adjust pH using citric acid to 5–6.

Example 7

Deep Conditioner Formulation with Vegetable Protein

| Ingredient | % w/w |
|---|---|
| Phase A | |
| Water, deionized | 75.50 |
| Phase B | |
| Cetaryl alcohol and Cetareth-20 | 6.00 |
| Cyclomethicone and Dimethiconol and Dimethicone | 1.00 |
| Lauryl Pyrrolidone | 0.50 |
| Phase C | |
| Water, deionized | 10.00 |
| Example 3 or 4/Present Invention | 2.00 |
| Phase C | |
| Propylene glycol and diazolidinyl urea and methyl paraben and propyl paraben | 1.00 |
| Phase D | |
| Hydrolyzed whole wheat protein | 2.00 |
| Phase E | |
| Fragrance as needed | 2.00 |
| Total | 100.00 |

Procedure

Heat Phase A to 70–75° C. with agitation. In a separate vessel, heat Phase B to 70–75° C. unitl melted. Add B to A with agitation. Cool to 50° C. add Phase C and D with stirring. Allow to cool to room temperature. Then add Phase E, if needed, with stirring.

Example 8

Conditioning Color-enhancer Shampoo Formulation

| Ingredient | % w/w |
|---|---|
| Phase A | |
| Laureth 8 and cocotrimonium chloride and butoxyethanol and PEG-7 glyceryl cocoate and quaternium 80 | 8.00 |
| Phase B | |
| Semi permanent hair dyes | qs |
| Phase C | |
| Water, deionized | qs to 100.00 |
| Phase D | |
| Sodium Laureth sulfate, 28% | 8.00 |
| Phase E | |
| Cocamide DEA | 4.00 |
| Sodium lauroyl sarcosinate | 15.00 |
| Phase F | |
| Example 3 or 4/Present Invention | 2.00 |
| Imidazonyl urea and methylparaben and propyl paraben sodium salt | 0.3 |
| Phase G | |
| Citric acid, to pH 5 to 6 | qs |
| Total | 100.00 |

Procedure

Dissolve Phase B in Phase A under stirring. Heat Phase C to 70–80° C.; add to AB. Add D, then E slowly. When homogeneous, under cooling to about 50° C. add Phase F. Adjust pH with citric acid to 5–6.

Example 9

Sun Protection Lotion

| Ingredient | % w/w |
|---|---|
| Phase A | |
| Glyceryl stearate citrate | 3.00 |
| Glyceryl laurate/citrate/lactate | 5.00 |
| Caprylic/Capric triglyceride | 16.00 |
| Octylmethoxy cinnamate | 7.00 |
| Microfine Titanium dioxide coated with alumina & simethicone | 3.00 |
| Phase B | |
| Example 3 or 4 | 2.00 |
| Water | 5.00 |
| Phase C | |
| Xanthan gum | 0.50 |
| Preservative | 1.00 |
| Water | Qs to 100.00 |

Procedure

Heat Phase A to approximately to 75° C. Stir Phase B; heat to 75° C. Add B to A with stirring. Homogenize and cool down the temperature to about 50° C. and add Phase C.

Example 10

Hair Color Fading Resistance Against UV Light

The UV photoprotection of hair color is tested for the product obtained from Example 3 vs a control formulation without the cationic sunscreen. The lightness and color changes of auburn-dyed hair have been measured over time of UV-B radiation by using X-Rite L a b instrument. $\Delta E$ (Lightness) and $\Delta C$ (color changes) are calculated by the following equation:

$$\Delta E = [(\Delta L)^2 + (\Delta a)^2 + (\Delta b)^2]^{1/2}$$

$$\Delta C = [(\Delta a)_2 + (\Delta b)^2]^{1/2}$$

The variables $\Delta L$, $\Delta a$ and $\Delta b$ are well known, as described in RG Kuehni, CIELAB Color Difference and Lightness, Hue and Chroma Components for Objective Color Control, Detroit Color Council, Technical bulletin No. 1; A Guide to Understanding Color Tolerancy, X-Rite Product Brochure, Grandville, Mich. 49418.

Two samples of hair were irradiated: S—hair swatches treated with formulation containing Example 3 and C—hair swatches treated with formulation without cationic sunscreen.

Results show treated hair with cationic sunscreen (example 3) has less color changes, both graying and color shift, than for the control.

The preceding examples can be repeated with similar success by substituting the generically or specifically described reactants and/or operating conditions of this invention for those used in the examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound of Formula I

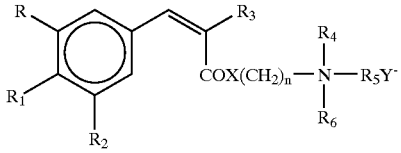

Formula I wherein one of R and $R_1$ is hydrogen or linear or branched $C_1$ to $C_{10}$ alkyl, or linear or branched $C_1$ to $C_{10}$ alkoxy and the other is independently linear or branched $C_1$ to $C_{10}$ alkyl, or linear or branched $C_1$ to $C_{10}$ alkoxy;

$R_2$ is linear or branched $C_1$ to $C_{10}$ alkyl, or linear or branched $C_1$ to $C_{10}$ alkoxy;

$R_3$ is selected from the group consisting of $COCH_3$, $CO_2R_7$, $CONH_2$, $CON(R_8)_2$, $COX(CH_2)n-N-(R_4)(R_5)(R_6)$, and the quaternized salt form of the formula $COX(CH_2)n-N-(R_4)(R_5)(R_6)^+Y^-$;

X is O or NH;

n is an integer of 1 to 5;

Y is an anion;

$R_4$, $R_5$ and $R_6$ are independently linear or branched $C_1$ to $C_{30}$ alkyl; and $R_7$ and $R_8$ are independently hydrogen or linear or branched $C_1$–$C_{30}$ alkyl.

2. A compound of Formula II:

Formula II

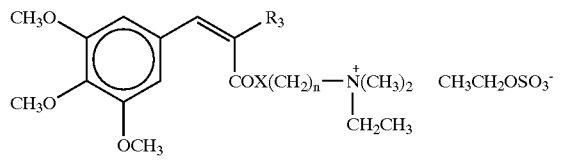

wherein $R_3$ is selected from the group consisting of $COCH_3$, $CO_2R_7$, $CONH_2$, $CONH(R_8)_2$, $CN$, $COX(CH_2)n-N-(R_4)(R_5)(R_6)$, and the quaternized salt form of the formula $COX(CH_2)n-N-(R_4)(R_5)(R_6)^+$; and wherein X is O or NH.

3. A compound of claim 2 wherein $R_3$ is $COCH_3$ or $CONH(CH_2)_3N^+(CH_3)_2(CH_2CH_3)CH_3CH_2OSO^-_3$.

4. A compound of claim 1 wherein X is O.

5. A compound of claim 1 wherein X is NH.

6. A compound of claim 1 wherein the integer n is 2 to 3.

7. A compound of claim 1 wherein the anion Y is selected from Cl, Br, alkyl sulfate, alkyl sulfonate, and p-tolyl sulfonate.

8. A compound of claim 1 wherein $R_6$ is independently linear or branched $C_1$ to $C_8$.

9. A sunscreen formulation comprised of a compound or a mixture of compounds of claim 2.

10. A sunscreen formulation comprised of a compound or a mixture of compounds of claim 1 capable of protecting against UV-B or UV-A rays or both UV-A and UV-B rays.

11. A compound of claim 2 wherein X is O.

12. A compound of claim 2 wherein X is NH.

13. A compound of claim 2 wherein the integer n is 2 to 3.

14. A compound of claim 1 wherein the anion Y is an alkyl sulfonate or alkyl sulfate.

15. A sunscreen formulation comprised of a compound or a mixture of compounds of claim 2 capable of protecting against UV-B or UV-A rays or both UV-A and UV-B rays.

16. A sunscreen formulation comprised of a compound or a mixture of compounds of claim 1 wherein at least one of the compounds of Formula I is capable of stabilizing the formulation against photodegradation.

17. A sunscreen formulation comprised of a compound or a mixture of compounds of claim 2 wherein at least one of the compounds of Formula II selected is capable of stabilizing the formulation against photodegradation.

18. A mixture comprised of at least one compound of claim 1 and at least one other sunscreen agent.

19. A mixture comprised of at least one compound of claim 1 and at least one additional sunscreen agent not of Formula I, wherein the compound of Formula I is capable of stabilizing at least one additional sunscreen agent against photodegradation.

20. A mixture comprised of at least one compound of claim 2 and at least one additional sunscreen agent not of Formula II, wherein the compound of Formula II is capable of stabilizing the at least one additional sunscreen agent against photodegradation.

21. A method of protecting a substrate from UV radiation which comprises applying a compound of claim 1 to the substrate.

22. A method as in claim 21 wherein the substrate protected from UV radiation is hair or skin.

23. A method as in claim 21 wherein the substrate protected from UV radiation is selected from the group consisting of polymers, textile fabrics, leathers and paints.

24. A method of protecting a substrate from UV radiation which comprises applying a compound of claim 2 to the substrate.

25. A method as in claim 24 wherein the substrate protected from UV radiation is hair or skin.

26. A method as in claim 24 wherein the substrate protected from UV radiation is selected from the group consisting of polymers, textile fabrics, leathers and paints.

27. A method of improving the photostability of a sunscreen formulation, the method comprising adding a compound of formula I of claim 1 to the formulation in an amount sufficient to improve the photostability of the formulation.

28. A method of improving the photostability of a composition consisting of sunscreen agents not of Formula I of claim 1, said method comprising adding a compound of formula I of claim 1 to said composition in an amount sufficient to improve the photostability of said composition.

29. A method of improving the photostability of a hair care formulation said method comprising adding a compound of formula II of claim 2 to the formulation in an amount sufficient to improve the photostability of the formulation.

30. A method of improving the photostability of a composition consisting of sunscreen agents not of Formula II of claim 2 said method comprising adding a compound of formula II of claim 2 to said composition in an amount sufficient to improve the photostability of said composition.

31. A compound of claim 1 in combination with a hairpiece.

32. A compound of claim 1 in combination with a substrate selected from the group consisting of polymers, textile fabrics, leathers and paints.

33. A compound of claim 2 in combination with a hairpiece.

34. A compound of claim 2 in combination with a substrate selected from the group consisting of polymers, textile fabrics, leathers and paints.

35. A compound of the following formula:

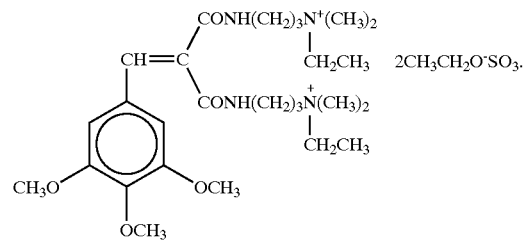

36. A compound of the following formula:

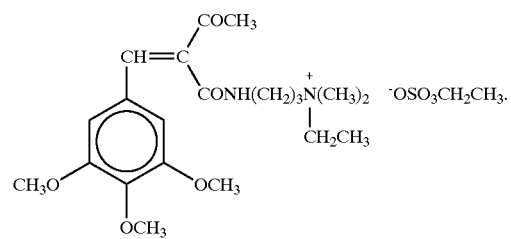

37. A compound of the following formula:

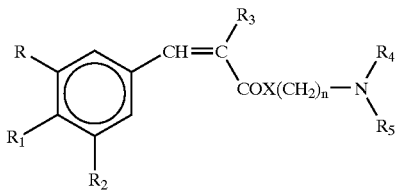

wherein,
one of R and $R_1$ is hydrogen or linear or branched $C_1$ to $C_{10}$ alkyl, or linear or branched $C_1$ to $C_{10}$ alkoxy and the other is independently linear or branched $C_1$ to $C_{10}$ alkyl, or linear or branched $C_1$ to $C_{10}$ alkoxy;

$R_2$ is linear or branched $C_1$ to $C_{10}$ alkyl, or linear or branched $C_1$ to $C_{10}$ alkoxy;

$R_3$ is selected from the group consisting of $COCH_3$, $CO_2R_7$, $CONH_2$, $CON(R_8)_2$, $CN$, $COX(CH_2)n-N-(R_4)(R_5)(R_6)$, and the quaternized salt form of the formula $COX(CH_2)n-N-(R_4)(R_5)(R_6)^+Y^-$;

X is O or NH;

n is an integer of 1 to 5;

Y is an anion;

$R_4$ and $R_5$ are independently linear or branched $C_1$ to $C_{30}$ alkyl; and $R_7$ and $R_8$ are independently hydrogen or linear or branched $C_1$–$C_{30}$ alkyl.

38. A compound of claim 37 wherein X is 0.

39. A compound of claim 37 wherein X is NH.

40. A compound of claim 37 wherein the integer n is 2 to 3.

41. A hair care formulation comprised of a compound or a mixture of compounds of claim 37 capable of protecting against UV-B or UV-A rays or against UV-A and UV-B rays.

42. A mixture comprised of at least one compound of claim 37 and at least one additional sunscreen agent not of Formula V.

43. A method of protecting a substrate from UV radiation which comprises applying a compound of claim 37 to the substrate.

44. A method as in claim 43 wherein the substrate protected from UV radiation is selected from the group consisting of polymers, textile fabrics, leathers and paints.

45. A compound of claim 37 in combination with a hairpiece.

46. A sunscreen formulation that comprises a compound of formula 1 in an amount effective to absorb illumination in a range above 290 nm wavelength, a cosmetically acceptable carrier and at least one cosmetic adjuvant selected from the group consisting of preservatives, antifoams, perfumes, oils, waxes, propellants, dyes, pigments, waterproofing agents, emulsifiers, surfactants, thickeners, humectants, exfoliants and emollients.

47. A personal care formulation as in claim 46 which is in a form selected from the group consisting of creams, ointment, suspensions, powders, oily lotions, oleo-alcoholic lotions, fatty gels, oleo-alcoholic gels, solid sticks, foams, emulsions, liquid dispersions, sprays and aerosols.

48. A sunscreen formulation as in claim 16 which additionally comprises an antioxidant selected from the group consisting of tocopherols, tocopherylacetate, Ascorbic acid, Emblica antioxidants, Proanthocyanidins, Rosemary antioxidants, green tea polyphenols, gallic acid, ellagic acid, butylhydroxy oxy toluene (BHT) and butylhydroxy anisole (BHA).

49. A sunscreen formulation that comprises a compound of formula 1 of claim 1 in an amount effective to absorb illumination in a range above 320 nm wavelength, a cosmetically acceptable carrier and at least one cosmetic adjuvant selected from the group consisting of preservatives, antifoams, perfumes, oils, waxes, propellants, dyes, pigments, waterproofing agents, emulsifiers, surfactants, thickeners, humectants, exfoliants and emollients.

50. A sunscreen formulation as in claim 48, which is in the form of lipsticks, foundation, make-up, loose or press powder, eye blush, eye shadows or nail lacquer.

* * * * *